(12) United States Patent
Luo

(10) Patent No.: US 11,903,644 B2
(45) Date of Patent: Feb. 20, 2024

(54) MEASURING EYE REFRACTION

(71) Applicant: The Schepens Eye Research Institute, Inc., Boston, MA (US)

(72) Inventor: Gang Luo, Lexington, MA (US)

(73) Assignee: The Schepens Eye Research Institute, Inc., Boston, MA (US)

( * ) Notice: Subject to any disclaimer, the term of this patent is extended or adjusted under 35 U.S.C. 154(b) by 850 days.

(21) Appl. No.: 16/971,981

(22) PCT Filed: Feb. 22, 2019

(86) PCT No.: PCT/US2019/019227
§ 371 (c)(1),
(2) Date: Aug. 21, 2020

(87) PCT Pub. No.: WO2019/165262
PCT Pub. Date: Aug. 29, 2019

(65) Prior Publication Data
US 2020/0397279 A1    Dec. 24, 2020

Related U.S. Application Data

(60) Provisional application No. 62/634,061, filed on Feb. 22, 2018.

(51) Int. Cl.
*A61B 3/032*    (2006.01)
*A61B 3/00*    (2006.01)
(Continued)

(52) U.S. Cl.
CPC ............ *A61B 3/032* (2013.01); *A61B 3/0025* (2013.01); *A61B 3/0091* (2013.01); *A61B 3/112* (2013.01);
(Continued)

(58) Field of Classification Search
CPC ...... A61B 3/0025; A61B 3/0091; A61B 3/032; A61B 3/112; A61B 3/113; G06T 7/74;
(Continued)

(56) References Cited

U.S. PATENT DOCUMENTS

| 9,549,669 | B2 | 1/2017 | Limon |
| 2017/0055827 | A1 | 3/2017 | Carrafa et al. |
| 2017/0079523 | A1 | 3/2017 | Limon |

FOREIGN PATENT DOCUMENTS

| WO | 2014/195951 A1 | 12/2014 |
| WO | 2019/165262 A1 | 8/2019 |

OTHER PUBLICATIONS

Pamplona, V et al. "NETRA: Interactive Display for Estimating Refractive Errors and Focal Range". MIT Media Lab [retrieved from the internet on Apr. 24, 2019]. Oct. 12, 2019 <URL: https://web.archive.org/web/20121012222344/http:/web.media.mit.edu/~pamplona/NETRA/Pamplona_et_al_SIGRAPH1010_low_res.pdf>; entire document, 9 pages.

(Continued)

*Primary Examiner* — Jack Dinh
(74) *Attorney, Agent, or Firm* — Quarles & Brady LLP

(57) ABSTRACT

Methods, systems, and devices are provided for measuring eye refraction without a lens, and more particularly, for measuring eye refraction with a mobile device application. An exemplary method includes measuring a distance between a patient and a mobile device, presenting to the patient one or more visual targets sized and shaped to represent perfect vision such as by using Vernier targets or grating targets, instructing the patient to indicate whether the patient can accurately read the visual targets and, if not, to move closer to the mobile device until the patient can accurately read the visual targets, calculating a vision prescription for the patient based on the visual targets and a final (Continued)

distance between the patient and the mobile device, and displaying the vision prescription for the patient.

13 Claims, 10 Drawing Sheets

(51) Int. Cl.
| | |
|---|---|
| *A61B 3/113* | (2006.01) |
| *A61B 3/11* | (2006.01) |
| *G06T 17/00* | (2006.01) |
| *G06T 7/73* | (2017.01) |
| *G02B 27/00* | (2006.01) |
| *G06K 9/00* | (2022.01) |
| *G06K 9/62* | (2022.01) |
| *G06V 40/19* | (2022.01) |
| *G06V 40/60* | (2022.01) |
| *G06V 40/16* | (2022.01) |
| *G06F 18/22* | (2023.01) |

(52) U.S. Cl.
CPC .......... *A61B 3/113* (2013.01); *G02B 27/0093* (2013.01); *G06F 18/22* (2023.01); *G06T 7/74* (2017.01); *G06T 17/00* (2013.01); *G06V 40/171* (2022.01); *G06V 40/19* (2022.01); *G06V 40/67* (2022.01)

(58) Field of Classification Search
CPC ...... G06T 17/00; G06V 40/171; G06V 40/19; G06V 40/67; G06F 18/22; G02B 27/0093
See application file for complete search history.

(56) References Cited

OTHER PUBLICATIONS

International Search Report and Written Opinion of International Application No. PCT/US2019/019227 dated Jul. 10, 2019, 15 pages.
Civera et al. (Oct. 2008) "Inverse Depth Parametrization for Monocular SLAM", IEEE Transactions on Robotics, 24(5):932-945.

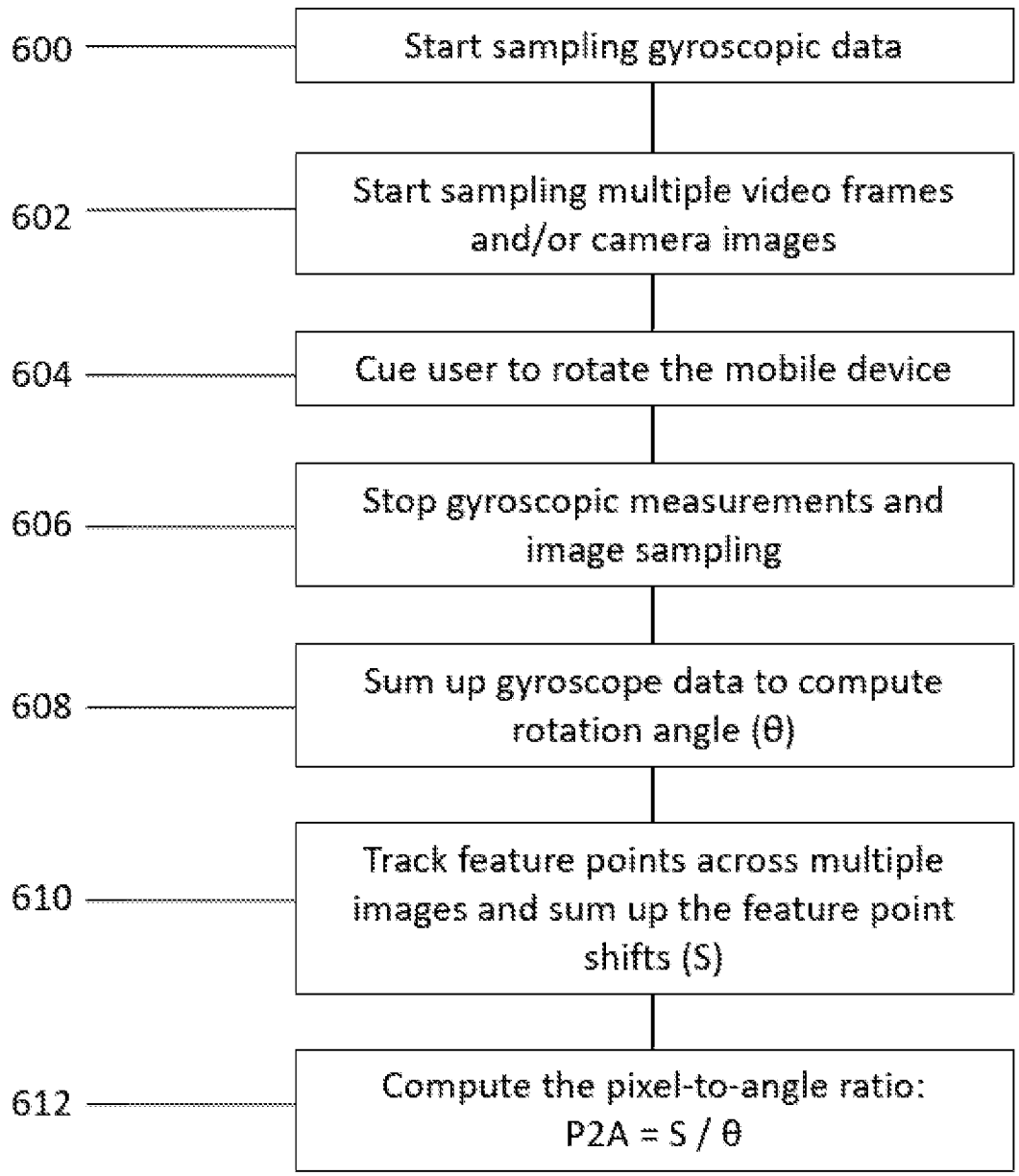

FIG. 8A
FIG. 8B
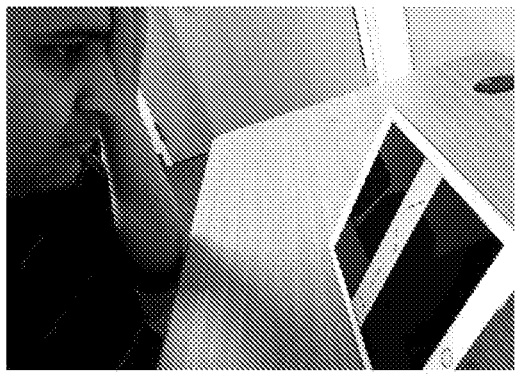
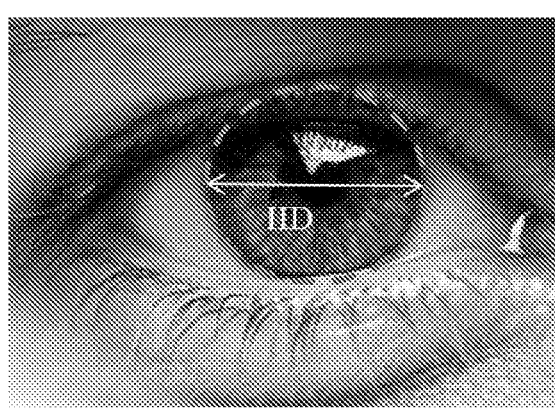
FIG. 9
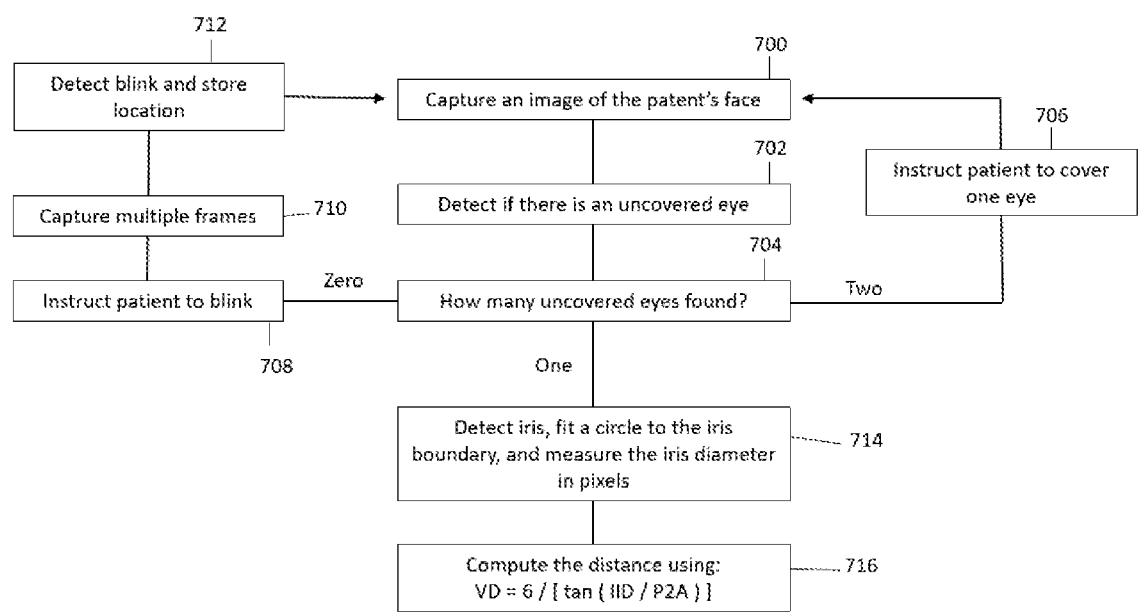

MEASURING EYE REFRACTION

RELATED APPLICATIONS

The present application is a national stage application of PCT/US2019/019227, which claims priority to U.S. Provisional Application 62/634,061 entitled "Measuring Eye Refraction" and filed on Feb. 22, 2018. The entire contents of these applications are incorporated herein by reference in their entirety.

FIELD

The present disclosure relates generally to measuring eye refraction without a lens, and more particularly, to a mobile device application for eye refraction measurement.

BACKGROUND

Generally, measuring eye refraction is a prolonged and relatively complicated process, requiring specialized equipment and specialized training. To receive a prescription for corrective lenses (Rx), a patient typically must go to an optometrist, or other specialized clinician to receive an eye refraction measurement. This test determines exactly what prescription a patient needs in his or her eyeglasses. The conventional refraction measurement method requires a clinician to place a patient at a fixed distance from visual stimuli, such as a sheet of letters of decreasing size known as an eye chart or a Snellen chart with optotypes. The clinician then repeatedly covers one eye with temporary correction lenses to figure out a prescription, resulting in the eyeglasses power needed for the stimulus image to be correctly focused on the retina of the patient. Conventional methods of carrying out the test include using trial refraction lenses, which are changed by clinicians manually, and auto-refractors, which automatically change lens power until the visual stimuli are focused. This is a long and expensive process, requiring a visit to a clinician and a multi-step test with specialized equipment to receive corrective lenses.

While attempts have been made to simplify this process, critical flaws exist in those approaches, resulting in limited use, measurement errors, and feasibility issues.

SUMMARY

Methods, systems, and devices are provided herein for measuring eye refraction without a lens, and more particularly, for measuring eye refraction with a mobile device application. For example in one exemplary embodiment, a method is provided that includes automatically measuring, by an image acquisition unit installed in a mobile device, a distance between a patient and the mobile device. The method also includes presenting, on a display of the mobile device, one or more visual targets sized and shaped to represent perfect vision. The visual targets can include Vernier targets or grating targets. A processor installed in the mobile device determines accurate sizes and shapes based on the measured distance. The method further includes instructing the patient to indicate whether the patient can correctly read the target or distinguish visual targets among other non-target stimuli and, if not, to move closer to the mobile device until the patient can correctly identify the visual targets. The method also includes automatically measuring, by the image acquisition unit installed in a mobile device, the distance between the patient and the mobile device again at a final distance at which distance the patient can accurately identify the visual targets. The method includes calculating, by the processor, a vision prescription for the patient based on the visual targets and a final distance between the patient and the mobile device. The method further includes displaying, by the display, the vision prescription for the patient.

The method can have numerous variations. For example, the patient can be required to accurately identify the misaligned Vernier targets. The visual targets can also include grating patterns at different frequency, contrast, and orientation, in which the patient can be required to detect the grating pattern among other gray patches. For example, the patient can be asked to accurately identify which of a plurality of stimuli has a grating pattern relative to the remaining plurality of stimuli that are gray patches. Automatically measuring the distance can include computing a pixel-to-angle ratio based on image analysis. Automatically measuring the distance can also include sampling, by the processor, gyroscopic data from the mobile device and sampling images from the image acquisition unit; instructing, by the mobile device, the patient to rotate the mobile device; computing, by the processor, a rotational angle based on the sampled gyroscopic data and the rotation of the mobile device; tracking, by the processor, feature points across multiple images and determining feature point shifts based on the tracked feature points; and computing, by the processor, a pixel-to-angle ratio based on the feature point shifts and the rotational angle.

The method can also include capturing an image of a face of the patient. In another example, automatically measuring the distance can include capturing an image of an iris of the patient. Automatically measuring the distance can also include capturing, by the image acquisition unit, an image of an eye of the patient; determining, by the processor, if an iris is present in the image; measuring, by the processor, a diameter of the iris; and computing, by the processor, the distance between the patient and the mobile device based on the measured diameter of the iris of the patient. In another example, measuring, by the processor, the diameter of the iris can further include fitting a circle to a boundary of the iris.

In another embodiment, the method can include prior to automatically measuring the distance, instructing, by the mobile device, the patient to create a 3D model of a face of the patient and save the 3D model to the mobile device. Automatically measuring the distance can also include capturing a current face image of the patient by the image acquisition unit; and measuring, by the processor, the distance between the patient and the mobile device by comparing the current face image to the 3D model of the patient stored on the mobile device. In another example, automatically measuring the distance can include capturing, by the image acquisition unit, a current face image of the patient; detecting, by the processor, one or more facial features on the current face image; calculating, by the processor, an overall inter-feature distance in pixels of each of the current face image and the 3D model; calculating, by the processor, an inter-feature distance ratio between the inter-feature distance of each of the current face image and the 3D model; and calculating, by the processor, the distance between the patient and the mobile device based on information in the 3D model and the inter-feature distance ratio.

In another aspect, a method is provided that includes presenting, on a display of the mobile device, one or more misaligned Vernier targets sized and shaped to represent good vision. A processor installed in the mobile device determines accurate sizes and shapes based on the distance between the patient and the mobile device. The method includes instructing, by the mobile device, the patient to indicate to the mobile device through one or more input units on the mobile device whether the patient can accurately identify the one or more misaligned Vernier targets. If the patient can correctly identify the one or more misaligned Vernier targets, the method includes instructing, by the mobile device, the patient to that a vision prescription for the patient is not required. If the patient cannot correctly identify the one or more misaligned Vernier targets, the method includes instructing, by the mobile device, the patient to move closer to the mobile device until the patient can accurately identify the one or more misaligned targets, and calculating, by the processor, the vision prescription for the patient based on the visual targets and a distance between the patient and the mobile device.

The method can have numerous variations. For example, determining the distance between the patient and the mobile device can include measuring the distance automatically by the mobile device. Determining the distance between the patient and the mobile device can alternatively include manually measuring the distance by the patient and inputting the distance into the mobile device by the patient through one or more input units on the mobile device. The mobile device can be one of a mobile phone, a tablet computer, or a laptop computer. Determining the distance can also include computing, by a camera and the processor of the mobile device, a pixel-to-angle ratio based on the mobile device and images of a room in which the method is performed. Determining the distance can include capturing an image of a face of the patient by a camera of the mobile device. Determining the distance can also include capturing an image of an iris of the patient by a camera of the mobile device. The method can further include prior to determining the distance, instructing, by the mobile device, the patient to create a 3D model of a face of the patient and save the 3D model to the mobile device. Determining the distance can then include capturing a current face image of the patient by a camera connected to the mobile device, and measuring, by the processor of the mobile device, the distance between the patient and the mobile device by comparing the current face image to the 3D model of the patient stored on the mobile device.

In another aspect, a device for vision prescription measurement is provided that includes at least a housing, an image acquisition unit disposed in the housing and configured to automatically measure a distance between a patient and the housing, a display, and a processor. The display is on at least part of an external surface of the housing, and the display is configured to present one or more visual targets sized and shaped to represent perfect vision. The visual targets include Vernier targets. The processor is disposed in the housing, and it is configured to determine accurate sizes and shapes of the one or more visual targets based on the measured distance. The display is further configured to instruct the patient to indicate whether the patient can accurately read the visual targets and, if not, to move closer to the housing until the patient can accurately read the visual targets. The image acquisition unit is also configured to automatically measure the distance between the patient and the housing at least one additional time at a final distance at which distance the patient can accurately read the visual targets. The processor is additionally configured to calculate a vision prescription for the patient based on the visual targets and the final distance between the patient and the mobile device, and the display is configured to then display the calculated vision prescription.

BRIEF DESCRIPTION OF THE DRAWINGS

The invention will be more fully understood from the following detailed description taken in conjunction with the accompanying drawings, in which:

FIG. 7 illustrates one embodiment of a procedure for computing a pixel-to-angle ratio, as used herein;

FIG. 8A illustrates an example scenario in which an image of a patient's eye is captured by the mobile device described herein;

FIG. 8B illustrates an example image of a patient's eye being processed by the mobile device application described herein;

FIG. 9 illustrates one embodiment of a procedure for measuring a distance between a patient and the mobile device described herein using an iris of the patient;

Figure 1:
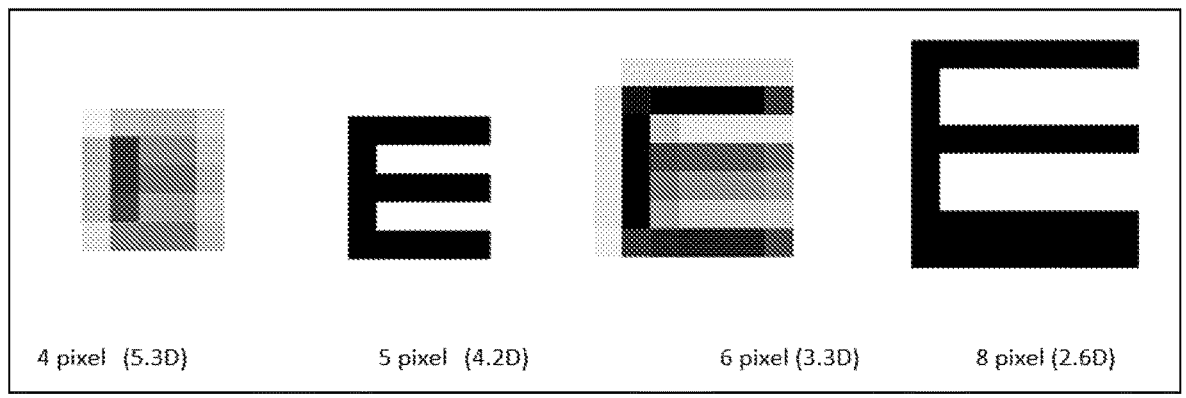
FIG. 1 illustrates optotype letters that cannot be displayed correctly when using eye refraction measurement methods.

The patent or application file contains at least one drawing executed in color. Copies of this patent or patent application publication with color drawing(s) will be provided by the Office upon request and payment of the necessary fee.

It should be understood that the above-referenced drawings are not necessarily to scale, presenting a somewhat simplified representation of various preferred features illustrative of the basic principles of the disclosure. The specific design features of the present disclosure, including, for example, specific dimensions, orientations, locations, and shapes, will be determined in part by the particular intended application and use environment.

DETAILED DESCRIPTION

Hereinafter, embodiments of the present disclosure will be described in detail with reference to the accompanying drawings. As those skilled in the art would realize, the described embodiments may be modified in various different ways, all without departing from the spirit or scope of the present disclosure. Further, throughout the specification, like reference numerals refer to like elements.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. The term "coupled" denotes a physical relationship between two components whereby the components are either directly connected to one another or indirectly connected via one or more intermediary components.

It is understood that the term "mobile device" or other similar term as used herein is inclusive of any portable computing device, such as smart phones, tablets, laptops, PDAs, and the like. A "mobile device," as used herein, is not necessarily limited to devices that are conveniently portable, but may also include personal computers (PCs) or other similar computing machines. As referred to herein, a "mobile device" is equipped with, at least, one or more processors, as is generally known in the art, and an image acquisition unit (e.g., camera) allowing for a user to capture a photograph of a given subject. Further, a "mobile device" is preferably equipped with communication components, either wired or wireless, allowing for the device to communicate with external devices via a communication network. Similarly, the terms "mobile device application," "mobile application," or "application," as used herein, refer to a computer program executable by a processor installed in a "mobile device," as is generally known in the art.

It is also understood that the term "patient" or other similar term as used herein is inclusive of any subject—human or animal—on which an ocular assessment could be performed. The term "user" as used herein is inclusive of any entity capable of interacting with or controlling a mobile device. The "user" may also be the "patient," or the "user" and "patient" may be separate entities, as described herein.

Additionally, it is understood that one or more of the below methods, or aspects thereof, may be executed by at least one processor. The processor may be implemented in a mobile device, as described herein. A memory configured to store program instructions may also be implemented in the mobile device, in which case the processor is specifically programmed to execute the stored program instructions to perform one or more processes, which are described further below. Moreover, it is understood that the below methods may be executed by a mobile device comprising the processor, in conjunction with one or more additional components, as described in detail below.

Furthermore, the methods, or aspects thereof, of the present disclosure may be embodied as non-transitory computer readable media on a computer readable medium containing executable program instructions executed by the processor. Examples of the computer readable mediums include, but are not limited to, ROM, RAM, compact disc (CD)-ROMs, magnetic tapes, floppy disks, flash drives, smart cards and optical data storage devices. The computer readable recording medium can also be distributed in network coupled computer systems so that the computer readable media is stored and executed in a distributed fashion, e.g., by a telematics server or a Controller Area Network (CAN).

When determining a prescription for a patient, one process that does not require any optical lens is to vary a viewing distance from which a patient views an object used to measure a prescription, and this process can be used to achieve a similar beneficial result to using a prescription process that uses lenses. In optics and optometry, rather than varying an actual distance to an object, a negative lens can be used to form an image of an object at a distance that is near to a patient for an object that is actually far away from the patient. Because of this, moving the object closer to the patient is generally similar to having a negative lens that would be able to produce such an image. However, when trying to implement a prescription-measuring process based on this distance-varying mechanism, both measuring the distances involved (especially in refraction measurements) and presenting visual stimuli close to a patient (or at a near distance) that is equivalent to an object that would normally be farther away from a patient (or at a far distance) present challenges. In some cases, manually measuring distances using a ruler or the like can be attempted. However, manually measuring distances can be inaccurate, time-consuming, and require expertise and know-how that limits its usefulness. Simply moving a vision chart from far away from a patient to a closer distance is inaccurate because angular letter sizes on the vision chart become larger as the vision chart is moved. Visual discrimination generally refers to the ability to recognize details in visual images, and for refraction measurement purposes used in this distance-varying process, consistent demand on visual discrimination should be maintained for all distances. For example, if a larger angular size is used for a closer distance, refraction error will be under-estimated because the demand is lower than on objects that are at a farther distance. In other words, achieved visual acuity in refraction measurement should be the same for farther distances and nearer distances.

In one approach, a prescription can be calculated as the reciprocal of Maximum Distance of Best Visual Acuity (MDBA). However, problems remain in the prior art when implementing this principle in systems using bitmapped displays (or raster displays). For example, U.S. Pat. No. 9,549,669 to Limon ("Limon") discusses measuring refractive error of an eye based on subjective distance metering. However, the approach taken in Limon suffers from some fundamental flaws that result in limited feasibility. As a few non-exhaustive examples, Limon uses optotype letters as a visual target for retraction measurement. See, e.g., U.S. Pat. No. 9,549,669 to Limon, FIG. 4F, FIG. 13A. This approach is a problem because it limits the number of prescriptions that can be accurately determined. For example, if a myopic or nearsighted patient needs his vision corrected to 20/16 vision, 20/16 letters should be used to estimate the Maximum Distance of Best Visual Acuity (MDBA). Assuming the patient needs a 4.2 D lens to see 20/16 letters, the MDBA would be 0.238 m, and the linear size of 20/16 letter E should be 0.387 mm, or exactly 5 pixels on a standard 458 PPI display (such as is used on the iPhone X). The optotype letter E can be shown correctly using 5 pixels, as it is comprised of 3 horizontal strokes in black pixels and 2 gaps in between in white pixels, as illustrated in FIG. 1. Similarly, the letter E can be shown correctly for a prescription of 2.1 D because the linear letter size should be 10 pixels at an MDBA of 0.476 m. However, using the approach in Limon, any required prescription that does not perfectly map to this 5-pixel factor requirement will require image scaling that causes distortion of the optotype. As an example, anyone who needs a prescription of 3.3 D, a 20/16 letter E would be 6 pixel high. It is not possible to show a 1.2 pixel wide stroke. Typically, graphic rendering will make the letter either blur or one of the stroke 2 pixel wide. As a result, the Limon method cannot measure prescriptions other than 4.2 D and 2.1 D correctly. If the screen resolution is lower than 458 PPI, the MDBA corresponding to 5 pixel letters will be larger than 0.238 m. This means the highest prescription that Limon's method can measure will be lower than 4.2 D. Thus, using the approach described in Limon would result in many prescriptions being measured incorrectly.

Limon also discusses measuring the viewing distance to a camera that most people cannot carry out without specialized knowledge. Limon discusses using a reference target with a known size, and Limon discusses that, to estimate a distance based on a reference target, the camera ratio should be given, which means providing the EFL/Pitch. The EFL is the camera effective focal length of camera lens, and the pitch is the physical distance between adjacent pixels on image sensor. These numbers vary across different cameras and are not known to most people.

Figure 2:
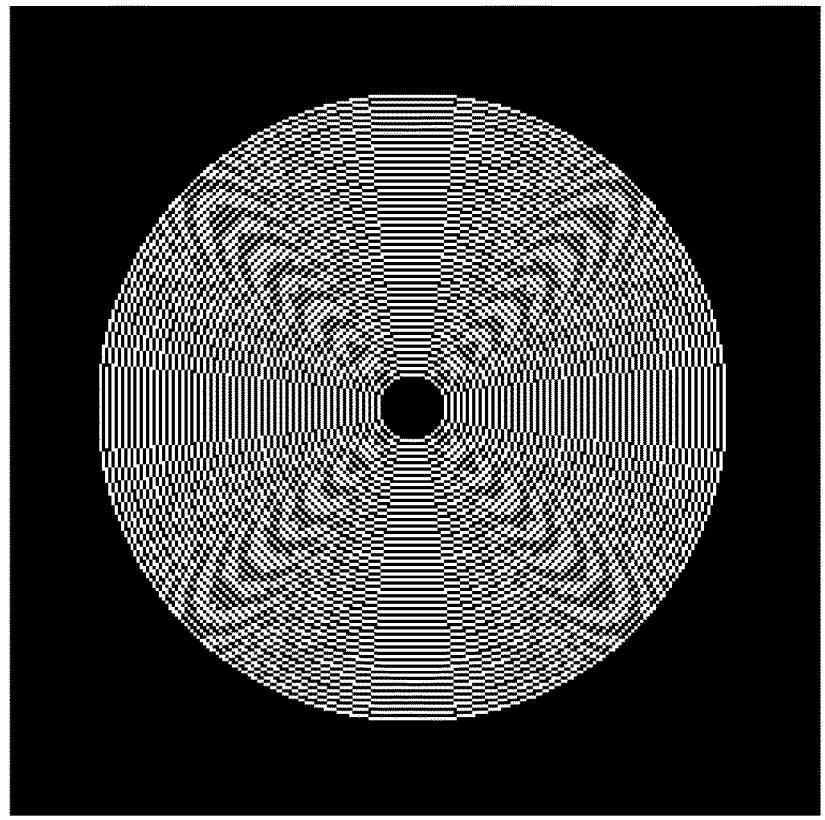
FIG. 2 illustrates artifacts on a concentric pattern used in various eye measurements.

Limon further discusses measuring astigmatism using concentric ring pattern. The illustrative figures, such as FIG. 4J of Limon, use low spatial frequency. This means that, when a patient sees these patterns, the patterns do not actually represent the patient's best corrected acuity. Therefore, the distance at which the patient can clearly see these low spatial frequency patterns is not actually the patient's correct MDBA. For instance, using again a sample patient who wants to achieve 20/16 corrected visual acuity, the spatial frequency he can see should be 37 cycles per degree. For a patient who needs a prescription of 4.2 D, for example, the distance from eye to screen in order to see the concentric pattern would be 0.24 m or closer. At this distance, each ring of the concentric pattern would be 1 pixel wide on a 458 PPI display or even less on a lower-resolution screen, which is not possible. When the ring width is only 1 pixel wide, some artifacts will appear on the image, as illustrated in FIG. 2. The fundamental reason causing the artifacts is that, along the diagonal direction, the spatial frequency is 1.414 times the horizontal or vertical frequency, and thus cannot be displayed correctly because it is not an integer. The screen resolution (i.e. screen spatial frequency) is just 2 times the ring in the horizontal or vertical directions. According to the Nyquist theorem, the screen resolution is just large enough for the concentric pattern to be correctly shown along the horizontal and vertical directions, but it is not enough to be shown correctly along the diagonal direction. This results in aliasing, which causes an artifact pattern. In other words, for anyone who wants to achieve a correct result from their eye test, the screen resolution of common mobile devices is not high enough to use the methods taught in Limon. The human eye cannot see a single pixel. If it could, people would see pixelated images on their screens. The refraction power that Limon's method can correctly measure is consequently limited to low end and not very accurate corrected vision because a low spatial frequency pattern has to be used.

Because of these and other reasons, the approach in Limon is not effective for many people that need an easy way to measure their eye refraction without having to go to the expense and trouble of visiting a clinician. Thus, while attempts have been made to simplify the prescription determination process, critical flaws exist in current approaches, resulting in limited use, measurement errors, and feasibility issues. Therefore, methods, devices, and systems are needed for measuring eye refraction without a lens, and more particularly, for a mobile device application for eye refraction measurement.

Referring now to embodiments of the present disclosure, measuring eye refraction is something that affects the majority of the adult United States population and many more internationally, with many people receiving some form of eye refraction measurement throughout their adult life. Even people who do not suffer from any type of impaired vision often receive eye exams throughout their life to confirm that no vision correction is required, and people that do have some form of impaired vision often are required to receive yearly eye exams because many prescriptions for corrective lenses are only accepted for up to 1 year. Thus, the majority of adults and many children receive or should receive regular eye exams, requiring expensive equipment, prolonged examination, and costly fees.

To this end, techniques are disclosed herein relating to a mobile device application for measuring eye refraction. Without using external accessories or attachments, the mobile application can measure eye refraction based on basic interactions between a patient and equipment on the mobile device, such as the display and the camera. Instead of using refraction lenses, the approach disclosed herein determines prescription by measuring a distance at which a patient can see stimuli clearly. The distance between the patient and the stimuli is varied, and thus no correction lens is needed. This approach can be utilized by anyone in need of eye refraction measurement, and it is particularly useful for people who have myopia (nearsightedness), as explained in detail below.

Figure 3:
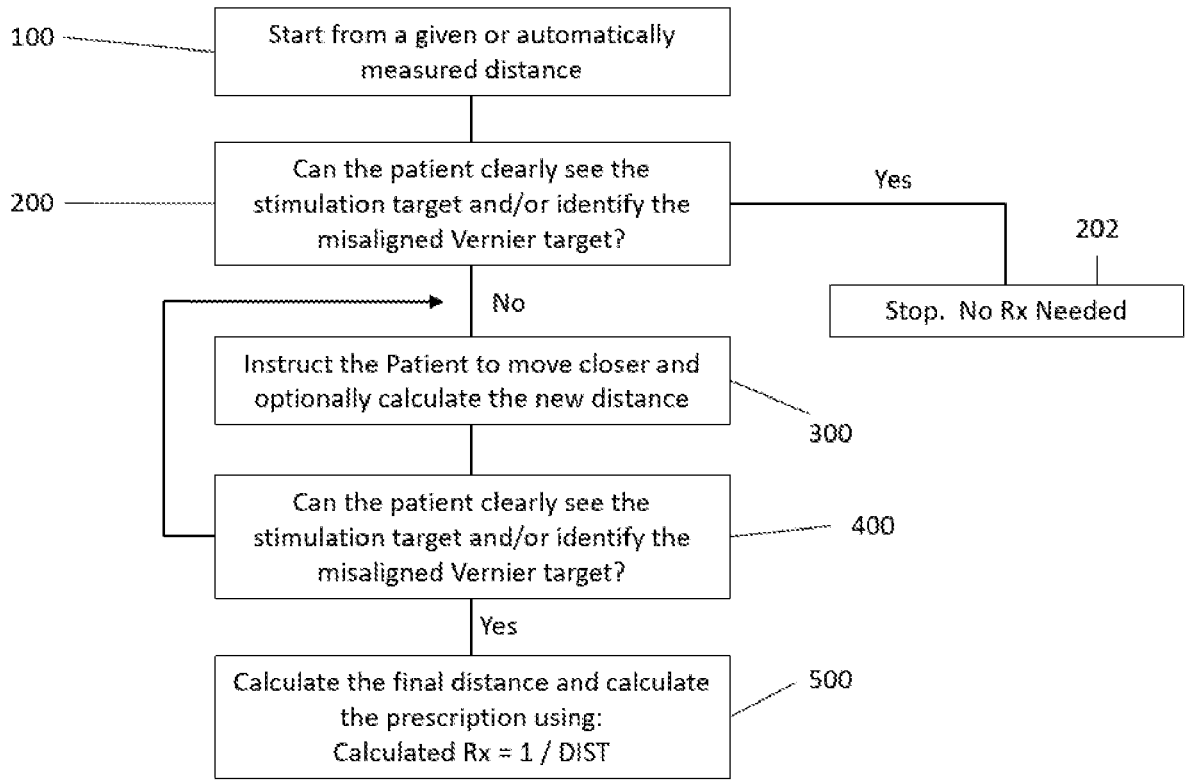
FIG. 3 illustrates one embodiment of a procedure for measuring eye refraction using a mobile device application described herein.

An exemplary method of the eye refraction measurement includes a patient starting from a given distance away from a mobile device that is running the application discussed herein at step 100, as illustrated in FIG. 3. The mobile device is configured to display visual stimuli that would indicate 20/20 or perfect vision, and the mobile device is arranged so that the patient can see the screen from the starting distance. The patient is then required to indicate if she can see the visual stimuli on the screen of the mobile device that would indicate 20/20 vision at step 200. If the patient can see the visual stimuli, the measurement will terminate because no prescription is required at step 202. If the patient cannot see the visual stimuli, the patient is required to reduce the distance between herself and the visual stimuli on the mobile device, for example by walking toward the mobile device, and the new distance between the patient and the mobile device can be calculated or measured at step 300. The patient then indicates whether she can see the visual stimuli at step 400. This process of observing the displayed visual stimuli and reducing the distance as needed to clearly see the stimuli is repeated until the patient can clearly see the visual stimuli on the mobile device. At this distance at step 500, the prescription for the patient is calculated by computing 1 divided by the distance in meters at which point the visual stimuli was clear. By taking advantage of high-resolution cameras installed in many modern mobile devices to calculate alignment and distance (discussed in detail below), in conjunction with the custom designed image processing algorithms described herein, a high accuracy of eye refraction measurement can be achieved. The entire processing is performed locally on the mobile device itself; thus, the application is not required to send any data to a remote server for processing. Based on the measurements taken, a highly accurate prescription can be calculated for the patient, especially for patients suffering from myopia for whom many other measurement methods currently on the market are not available.

Generally, prescriptions are provided by listing a value for each eye for a sphere and a cylinder. The sphere value indicates the amount of lens power, measured in diopters (D), prescribed to correct nearsightedness or farsightedness. If the number appearing under this heading has a minus sign, a patient is nearsighted, and if the number has a plus signor, a patient is farsighted. The term "sphere" indicates that the correction for nearsightedness or farsightedness is spherical, meaning that it is equal in all meridians of the eye. Cylinder indicates the amount of lens power needed to correct for any astigmatism of the patient. The number for the cylinder may be preceded with a minus sign (for the correction of nearsighted astigmatism) or a plus sign (for farsighted astigmatism). The term "cylinder" indicates that lens power added to correct astigmatism is not spherical, but instead is shaped so one meridian has no added curvature, and the meridian perpendicular to this "no added power" meridian contains the maximum power and lens curvature to correct astigmatism. An axis also is provided when astigmatism is detected. This number describes the lens meridian that contains no cylinder power to correct astigmatism. The axis is defined with a number from 1 to 180, in which the number 90 corresponds to the vertical meridian of the eye and the number 180 corresponds to the horizontal meridian. The meridian in the eye is a circle of constant longitude that passes through the iris of the eye. For example, if the circular eye was the face of a clock, a line connecting 12 o'clock and 6 o'clock would be one meridian, a line connecting 3 o'clock and 9 o'clock is another, etc.

Figure 4:
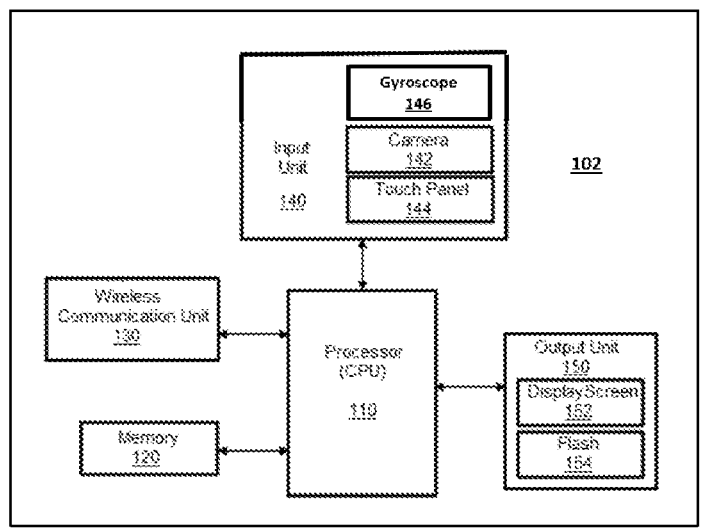
FIG. 4 illustrates an example diagrammatic view of a mobile device architecture.

FIG. 4 illustrates an example diagrammatic view of a mobile device architecture according to embodiments of the present disclosure. As shown in FIG. 4, a mobile device 102 may contain multiple components, including, but not limited to, a processor (e.g., central processing unit (CPU) 110, a memory 120, a wireless communication unit 130, an input unit 140, and an output unit 150. It should be noted that the architecture depicted in FIG. 4 is simplified and provided merely for demonstration purposes. In view of the wide variety of commercially available mobile devices, the architecture of the mobile device 102, which is referenced throughout the present disclosure, can be modified in any suitable manner as would be understood by a person having ordinary skill in the art, in accordance with the present claims. The mobile device architecture depicted in FIG. 4 should be treated as exemplary only and should not be treated as limiting the scope of the present disclosure.

Components of the mobile device 102 will be briefly described hereinbelow. The processor 110 is capable of controlling operation of the mobile device 102. More specifically, the processor 110 may be operable to control and interact with multiple components installed in the mobile device 102, as shown in FIG. 4. For instance, the memory 120 can store program instructions that are executable by the processor 110. The mobile application described herein may be stored in the form of program instructions in the memory 120 for execution by the processor 110. The wireless communication unit 130 can allow the mobile device 102 to transmit data to and receive data from one or more external devices via a communication network. The input unit 140 can enable the mobile device 102 to receive input of various types, such as audio/visual input, user input, data input, and the like. To this end, the input unit 140 may be composed of multiple input devices for accepting input of various types, including, for instance, a camera 142 (i.e., an "image acquisition unit"), touch panel 144, microphone, one or more buttons or switches, a gyroscope 146, and so forth. The input devices included in the input 140 may be manipulated by a user. For instance, a user can capture a photograph using the camera 142 by pressing the touch panel 144 in a recognized manner (i.e., a manner recognized by the processor 110). The camera 142 may include a front-facing camera. A rear-facing camera may be included in the camera 142, as well, but the front-facing camera will be primarily used herein. Notably, the term "image acquisition unit," as used herein, may refer to the camera 142, but is not limited thereto. For instance, the "image acquisition unit" may refer to a program that acquires an image of a patient stored locally in the memory 120 or remotely on a server. The output unit 150 can display information on the display screen 152 for a user to view. The display screen 152 can also be configured to accept one or more inputs, such as a user tapping or pressing the screen 152, through a variety of mechanisms known in the art. The output unit 150 may further include a flash producing device 154 (i.e., "flash") which is a light source capable of producing a beam of light. The flash producing device 154 can be configured to produce a flash of light during acquisition of an image by the camera 142.

The mobile device 102 can thus be programmed in a manner allowing it to perform the techniques for eye refraction measurement described hereinbelow.

In use, the patient should place the mobile device 102 at a location at which the patient can see the display screen 152 and be seen by the image acquisition unit, such as the camera 142. For example, the patient can place the mobile device 102 on a table, shelf, secured to a wall, etc. The application on the mobile device 102 requires the starting distance between the patient and the mobile device 102 to be known by the mobile device 102. To accomplish this, a patient can start at a known distance away from the mobile device 102, can provide the distance between the patient and the mobile device 102 to the mobile device 102, or the application can measure a distance between the mobile device 102 and the patient automatically through a variety of means. Throughout all of these measurement approaches and generally throughout the entire interaction between the patient and the application on the mobile device 102, the application can provide guidance in real-time for the user in the form of instructions and/or graphics 210 displayed on the display screen 152 to assist the user in proper measurement and use in general. The information received by the mobile device 102 from the patient through various inputs and by the camera 142 can then be proceed by the processor 110 to determine the distance between the patient and the mobile device.

The starting distance between the patient and the mobile device 102 can be a set distance, for example between about 2 to 40 feet, such as 8 feet, 10 feet, 12 feet, 14 feet, 16 feet, 18 feet, 20 feet, 22 feet, 24 feet, 26 feet, etc. A myopic patient often needs to be at a distance shorter than 6.1 meters (20 feet) in order to clearly see the visual stimuli representing 20/20 vision, for example 0.5 meters (1.64 feet). The spherically equivalent correction would be reciprocal of the distance, in this case 1/0.5=2D. Thus, about 20 feet is a generally used as a starting distance for patients using the application.

The starting distance between the patient and the mobile device 102 can also be provided to the mobile device 102 manually by the patient or a second party providing the distance through various mechanisms with the input unit 140, such as using voice commands, physically typing through the touch panel 144, remote controls, etc. The patient must be able to measure the distance using this approach, for example by using a tape measure.

Figure 5:
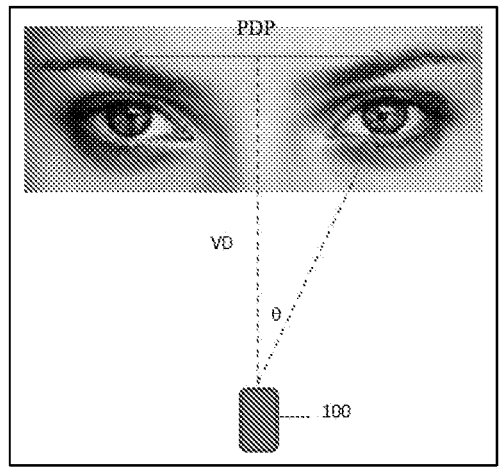
FIG. 5 illustrates an example view of the mobile device acquiring an image of eyes of a patient.

The starting distance can also be automatically measured by the application through use of the mobile device 102, the input unit 140 and/or the camera 142, and one or more suitable image processing algorithms known in the art, which is the preferred approach to make measurement easier for the patient. Throughout the discussion below, a variety of suitable image processing algorithms can be used, such as an adaptive thresholding algorithm, for example. There are a variety of different approaches through which the distance between the patient and the mobile device 102 can be measured. For example, as illustrated in FIG. 5, the application can measure the distance between the patient's two eyes (IPD) in an image and then calculate the distance using the following equation:

$$VD=PDP/\tan\theta$$

where VD is the viewing distance between the patient and the camera 142, PDP is the physical size of the intra-pupil distance (IPD), and $\theta$ is the spanning angle of half IPD.

For an individual patient, the PDP can be measured beforehand using a ruler or can be measured by processing a snapshot of the face of the patient, and calculated using:

$$PDP=(PDX/IRSX)\times 12$$

where PDX is the IPD in pixel units and IRSX is the iris diameter of the patient in pixel unit. The $\theta$ value in the equation above is in degree units. It is converted from pixels to angles through a pixel to angle converting factor P2A. The converting factor can be determined using measurements from the gyroscope 146 of the mobile device 102 and tracked image shifts when rotating the device, as explained below and illustrated in FIGS. 6 and 7.

Figure 6:
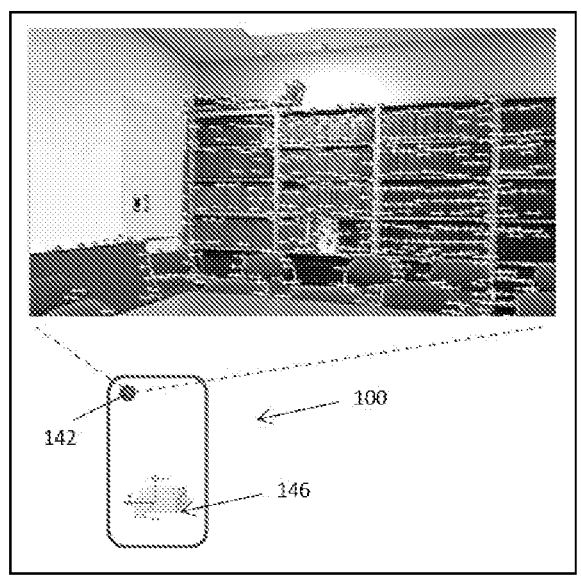
FIG. 6 illustrates an example image of the mobile device capturing a sequence of images for estimating the pixel-to-angle ratio.

As illustrated in FIGS. 6 and 7, the patient can determine $\theta$ and the converting factor from pixels to angles P2A through first pointing the camera 142 at objects in the room, preferably several meters away, for example between about 2 meters to about 20 meters, such as about 2 meters, 3 meters, 4 meters, 5 meters, etc. The mobile device 102 then starts sampling the gyroscopic data 146 at step 600 and starts sampling multiple video frames from the camera 142 at step 602. The patient can then slightly rotate the mobile device 102 so that images captured by the camera 142 will shift at step 604, as indicated by the shifting points illustrated in FIG. 6. Sampling of both the gyroscopic data 146 and the video frames from the camera 142 is then stopped at step 606. Using the data from when the mobile device 102 was shifting or rotating, the rotation angle 9 can be measured by the data from the gyroscope 146 at step 608. The amount of image shift (in pixel units) can be determined by object tracking or optical flow tracking, for example by tracking feature points across multiple images taken by the camera 142 and summing up the tracked feature points to determine the feature point shift S at step 610 using one or more algorithms known in the art. The pixel-to-angle converting factor is then determined by the feature point shift S over the rotation angle $\theta$ at step 612.

The operations herein will be largely automated in the application, requiring only that the user follow a few simple steps: first pointing the camera 142 at the user, possibly entering the manually-measured PDP in some approaches of the application, and pointing the camera 142 at objects several meters away and then shifting the camera 142. The application can automatically process images captured by the mobile device 102. Additionally, the PDP and the angle scale factors are determined and saved in the mobile device 102 as two constants for the patient and the mobile device 102. The process is only a one-time calibration when the application is first used, and does not need to be recalibrated (as a distance between the patient and the mobile device 102 continues to be utilized during use of the application).

Another method of determining viewing distance is possible that is similar to the approach above but does not include measuring PDP. This method may be particularly useful when the viewing distance is short. As illustrated in FIGS. 8A-9, the patient covers one eye and looks at stimuli on the display screen 152 of the mobile device 102 while the camera 142 captures images of the viewing eye at step 700 and the processor 110 processes the image. The method can include detecting if an uncovered eye is present in the image at step 702 and determining how many uncovered eyes are present at step 704. If two eyes are visible at step 704, the patient is instructed to cover one eye at step 706 either through the display screen 152 and/or speakers in the device 102, and if no eyes are visible at step 704, the method instructs the patient to blink at step 708 and proceeds to capture multiple images using the camera 142 at step 710 to determine if the patient was blinking. To help the device 102 successfully capture an image, the application can process the image to detect a blink and store a location of the blink in the image at step 712 so that, as another image is captured, the application can determine where an eye should be in the image. Once the method detects that only one eye is visible, a software sub-application running in the overall application on the device 102 processes the viewing eye image to extract the iris edge by fitting a circle to the iris boundary and measuring the iris diameter in pixels at step 714. The viewing distance can then be calculated at step 716 based on the diameter calculated from those images using the equation:

$$VD=6/[\tan(IID/P2A)]$$

where IID is the diameter of the patient's iris in pixel units, and P2A is the pixel to angle converting factor, which is determined based on the explanation above and in FIGS. 6 and 7. The patient can thus be instructed by the mobile device 102 or by a second person using the mobile device 102 to follow the steps above to allow the application to acquire the necessary information.

Figure 10:
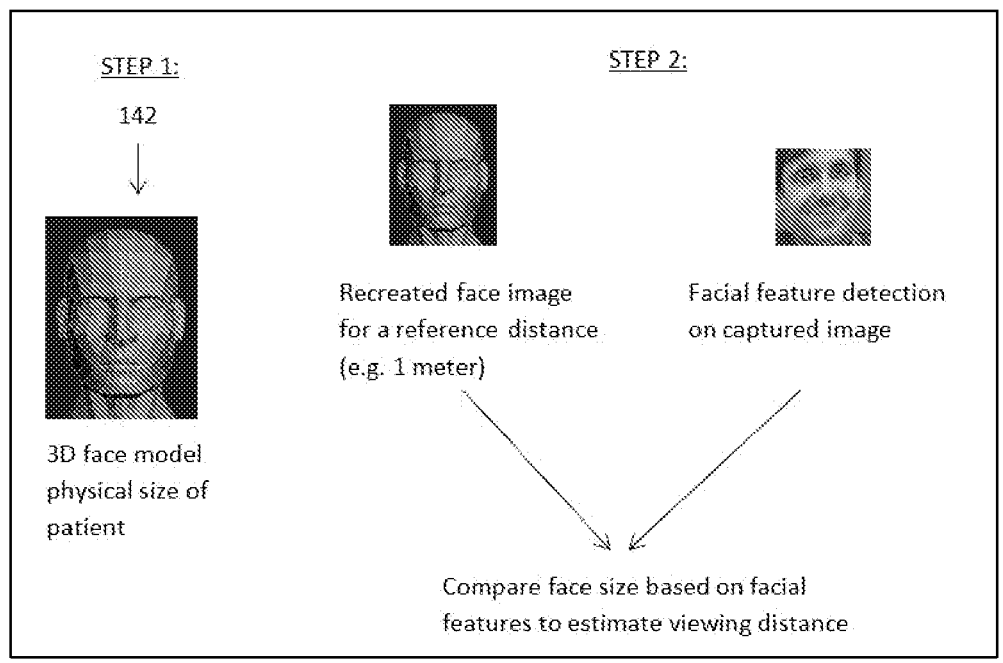
FIG. 10 illustrates another embodiment of a procedure for measuring a distance between a patient and the mobile device described herein using a 3D model of a face of the patient.
Figure 11:
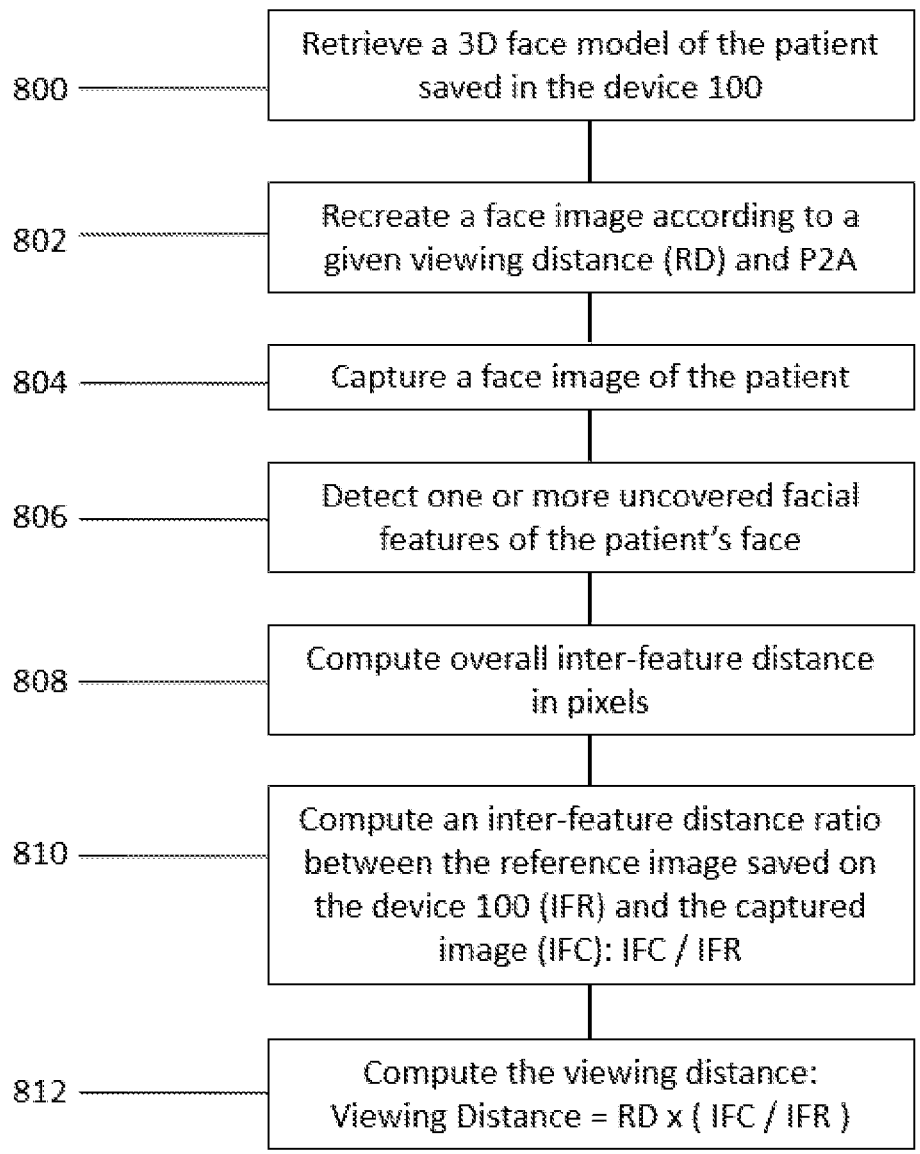
FIG. 11 illustrates the procedure of FIG. 10 for measuring a distance between a patient and the mobile device described herein using a 3D model of a face of the patient.

Another method used to measure the viewing distance is based on changes in the size of the patient's face as captured by the mobile device 102, as illustrated in FIGS. 10 and 11. Before using the application, the patient needs to create a 3D profile of his own face. The patient must point the camera 142 at his face and rotate the camera 142 around his face, taking multiple face pictures from different angles. Monocular SLAM (simultaneous localization and mapping) analysis can be performed to create the 3D profile of the patient's face. SLAM is a computer vision method that is commonly used in robotics, as discussed in J. Civera et al., "Inverse Depth Parametrization for Monocular SLAM," *IEEE Transactions on Robotics*, vol. 24, no. 5, pp. 932-945, October 2008, available at http://ieeexplore.ieee.org/stamp/stamp.jsp?tp=&arnumber=4637878&isnumber=4663225 and incorporated herein by reference in its entirety. In the paper, a real-time (30 Hz) fully automatic 3-D SLAM system was presented that featured a handheld single camera approach with no additional sensing. However, alternative 3D mapping methods can be used herein. For example, an alternative method to capture the 3D profile is through face ID cameras, such as those available in iPhone X.

The patient thus initially captures a 3D profile of his face. The application has a starting profile of the user's face with which to compare images taken during use. During use of the application, the application retrieves the 3D profile of the patient's face at step 800 and recreates a face image according to a given viewing or reference distance RD (such as at a distance of 1 meter) and the P2A (calculated as explained above) at step 802. The camera 142 then captures an image of the face of the patient in real time during use at step 804, and the application detects several facial features on the patient's face at step 806. The application then computes the overall inter-feature distances in pixels at step 808, and an inter-feature distance ratio is compared between the reference 3D profile that was initially provided by the patient and the captured image, resulting in the ratio of the captured inter-feature value IFC to the reference inter-feature value IFR at step 810. The distance is then calculated by multiplying the given viewing or reference distance RD by the ratio of the captured inter-feature value IFC to the reference inter-feature value IFR at step 812:

$$\text{Distance} = RD \times (IFC/IFR)$$

Thus the viewing distance is measured by first calculating the ratio between the face size at a given distance with the face size recreated according to the 3D face profile, and then multiplying the ratio by the given viewing distance of the recreated face. The recreated reference face orientation also needs to be matched to the captured face image during distance determination. Additionally, to minimize the error, the ratio calculated above can be the average of ratios for multiple facial feature pairs, for instance, distance from eye to nose, distance from mouth to eye, and distance between two eyes.

Through any one of the approaches discussed above, the application can determine a viewing distance between the patient and the mobile device 102.

After determining the viewing distance, the mobile device 102 is configured to display visual stimuli that would indicate 20/20 or perfect vision for that viewing distance. For example, the output unit 150 can display information on the display screen 152 for the patient, and the processor 110 can determine what to display. Thus the size of the visual stimuli being displayed can vary depending on the distance between the patient and the mobile device 102. For example, if the viewing distance is 2 meters and the visual stimuli is displayed at a standard 20/20 size accordingly and then the application determines that the patient has moved from 2 meters away to 1 meter away, the size of the visual stimuli can be reduced to half the previous standard 20/20 size so that the angular size of the visual stimuli will maintain 20/20. The measured viewing distance between the patient and the mobile device 102 can thus influence the size of the visual stimuli such that the application will change the displayed linear size according to the distance.

While the visual stimuli can take a variety of forms, one of the preferred approaches is to use Vernier stimuli. This is especially true when the patient suffers from myopia because myopic patients have to view the mobile device 102 from a short distance, and when the viewing distance is short, optotypes (such as Snellen letters) may not display properly, as discussed above regarding the problems with Limon. Therefore, Vernier stimuli (in high or low contrast) are preferably used.

Figure 12:
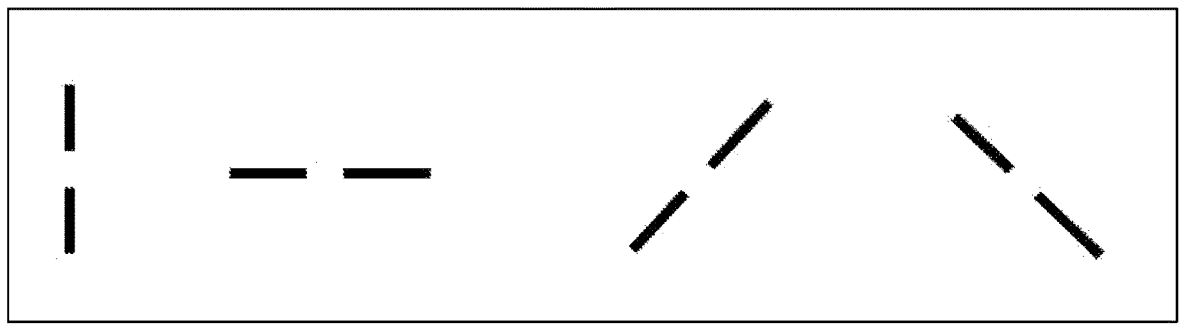
FIG. 12 illustrates an embodiment of high-contrast Vernier targets.
Figure 13:
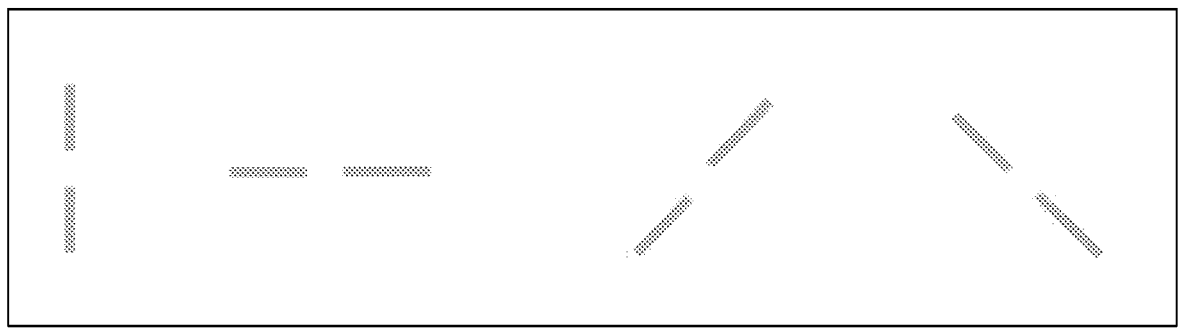
FIG. 13 illustrates an embodiment of low-contrast Vernier targets.

FIGS. 12 and 13 illustrate two examples of Vernier stimuli. The patient compares the stimuli shown in either FIG. 12 or FIG. 13 and indicates which one of the four Vernier targets is not aligned. The color of the target can be in high contrast, as in FIG. 12, or low contrast, as in FIG. 13. A low contrast target is more difficult to view for a patient, and the resulting refraction measurements will be more accurate.

During testing, the patient identifies the target that is not aligned. If the patient cannot identify the misaligned visual stimuli correctly, the patient is required to reduce the distance between herself and the visual stimuli on the mobile device 102, for example by walking toward the mobile device 102. For example, the output unit 150 can display shuffled stimuli on the display screen 152, and the application can determine whether the patient's response is correct. If the patient cannot identify the misaligned stimulus correctly, the application can communicate with the patient, for example through the display screen 152, through speakers in the device 102, etc., to move closer to the display device 102. At a closer distance, the patient then again reports which one is the misaligned visual stimuli. If she still cannot identify correctly, she again moves closer to the visual stimuli until the patient can clearly see the visual stimuli on the mobile device 102 and correctly identify the misaligned target. Each new distance can be automatically determined by the mobile device 102 using the approaches discussed above or can be manually entered by the patient or a second party. Furthermore, the processor 110 can receive input from the user and coordinate and process output by the application at each step.

Figure 14:
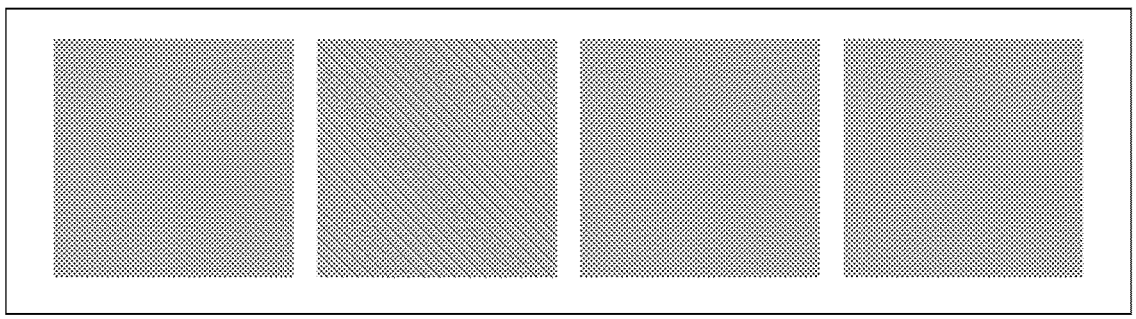
FIG. 14 illustrates an embodiment of grating targets with the first, third, and fourth boxes being gray patches and the second box having a grating pattern.

Another preferred testing approach is to use grating testing. FIG. 14 illustrates examples of targets used in grating testing, for example one or more boxes. FIG. 14 illustrates an exemplary embodiment with four boxes. One of the boxes has a grating pattern, while the remaining boxes have a flat, gray color. During testing, the patient identifies which stimulus has the grating pattern among the one or more other targets that are simple gray patches. Grating is a pattern that is marked or ruled with close parallel lines and is characterized by its spatial frequency, contrast, and orientation in such a way that patients without satisfactory vision will not be able to perceive grating in the target (which should appear as contrasting brighter and darker stripes) and instead will perceive the grating pattern target as a gray patch that is identical to the other targets presented. The overall brightness of the grating (which correspond to an average of the bright and dark stripes) is the same as the brightness of the gray patches. Unlike optotype letters or concentric patterns, the grating pattern will not be subject to distortion when the grating pitch is high because the pattern of the target is of straight lines. By definition, a person with 20/20 visual acuity should be able to see 30 cycles/degree grating in high contrast. When the resolution of a display screen of a mobile device is not high enough to show 30 cycles/degree grating, which is very likely at short viewing distances, the grating frequency can be lower than 30 cycles/degree. In such a situation, the grating contrast will be lowered as well without affecting a patient's ability to receive an accurate eye refraction measurement, for instance by lowering the grating contrast based on a contrast sensitivity function. Thus, the screen resolution will not prevent accurately displaying visual targets, and the approaches discussed herein can be used to accurately identify a prescription at which the patient can achieve good vision, such as 20/20 vision.

At the distance where the patient can clearly see the visual stimuli, the prescription for the patient is calculated by computing 1 divided by the distance at which point the visual stimuli was clear and/or the patient could correctly identify the misaligned target:

Calculated Rx=1/DIST where the Calculated Rx is the prescription of the patient and DIST is the distance in meters between the patient and the visual stimuli at which point the patient can clearly see the stimuli. The distance between the patient and the mobile device 102 is thus required to be known at least at the end of the eye refraction measurement, too. The distance can be determined through the methods provided above, for example manually or automatically. Additionally, the patient must be able to indicate that she can clearly see the visual stimuli (at which point the application ends the test) or optionally may be able to indicate that she cannot see the visual stimuli (at which point she can move closer to the mobile device 102). The indication that the patient can clearly see the visual stimuli can be manually provided to the mobile device 102 by the patient or a second party through various mechanisms with the input unit 140, such as using voice commands, physically typing through the touch panel 144, remote controls, etc. Real-time viewing distance updates is important for the application to determine accurate prescriptions, as detailed below. In other embodiments, different visual stimuli can be used, such as the grating pattern in FIG. 14, in which case the patient will continue to advance toward the mobile device 102 until she can clearly see each stimulation target.

By using the application provided herein with the preferred Vernier stimuli, astigmatism can also be diagnosed and measured. The astigmatism axis can be estimated based on the discrimination ability difference of the patient for multiple orientations of the Vernier stimuli. For example, a patient should have zero astigmatism if the patient has equal ability to detect misalignments of the Vernier stimuli across all orientations. If a patient struggles with identifying misalignment of stimuli along horizontal or vertical alignments, the patient suffers from astigmatism, and the astigmatism axis is likely close to horizontal or vertical. Additionally, if the astigmatism axis is close to horizontal or vertical, a patient's discrimination ability for misaligned diagonal targets should be about the same, and vice versa. The application can focus on identifying astigmatism even more precisely with more precise astigmatism axis estimations by using more orientations, which will give the application more data regarding the patient's struggles with identifying misalignment of stimuli and can thus provide more data for a more accurate estimate.

Once the astigmatism axis is determined for a patient using the approach above, the cylinder correction can be measured by changing a viewing distance until the perpendicular Vernier stimuli targets becomes clear. For instance, if the patient can see horizontal Vernier stimuli targets clearly at 0.25 meters but she needs to move to 0.2 meters to see vertical Vernier stimuli targets clearly, then her prescription can be determined by the application and method herein to be −4D spherical, −1D cylindrical, axis 90 degrees. Thus the Vernier stimuli can be used to identify and correctly prescribe astigmatism in patients, while other approaches (such as those taken in Limon) cannot. In this situation, it can thus important for the patient to provide ongoing data to the application rather than simply walking close enough to the mobile device 102 and determining a final distance. Here, the application can instruct the patient to provide ongoing feedback as the Vernier targets are changed and the patient moves closer and closer to the mobile device 102 so that the application can determine when vertical Vernier stimuli targets are clear compared to horizontal Vernier stimuli targets.

Similar to using Vernier stimuli, astigmatism can also be diagnosed and measured using grating patterns. The astigmatism axis can be estimated based on the discrimination ability difference for multiple orientations of the grating pattern. For example, a patient should have zero astigmatism if the patient has equal ability to see the grating in all orientations. During testing, if a patient struggles with identifying grating along horizontal or vertical alignments, the patient suffers from astigmatism, and the astigmatism axis is likely close to horizontal or vertical. The application can thus take this information into considering when determining a prescription for the patient.

As discussed above, the current approach to measuring eye refraction as detained herein is beneficial over the prior art, such as Limon, for several reasons. For example, as previously discussed, Limon uses optotype letters as targets, which can cause distortion of the targets depending on the resolution of the display of the mobile device being used and the prescription needed. The application discussed herein is able to eliminate this problem by using Vernier targets or grating targets. The Vernier target consists of two short lines that are either aligned or slightly misaligned. During testing, the patient identifies the stimulation target that is not aligned. By using this stimulation approach instead of a more common approach, such as optotype letters, is that the line width and the misalignment in terms of pixel can be any integer. There is thus no distortion when displaying stimuli, and as testing results show below, the approach provided herein can measure refraction from 0 to 7 accurately. That is not possible using optotype letters on existing mobile device displays. Additionally, distance measurement between a patient and a mobile device is simpler in the application provided here than in the prior art, such as Limon. As discussed, Limon teaches using a reference target with a known size and a calibration method requiring that a patient provide the camera ratio of EFL/Pitch. Again, most consumers with mobile devices do not know these values. Here to the contrary, multiple methods are provided and can be used to estimate the viewing distance, many of which are automatic and easier for a patient to carry out. Furthermore, the prior art does not provide effective methods of estimating astigmatism. As discussed above, Limon teaches a method of measuring astigmatism using concentric ring patterns that will not display correctly on most mobile devices. The screen resolution of common mobile devices is simply not high enough to achieve good astigmatism prescriptions. As described above, though, the approach used by the application provided herein results in very accurate astigmatism measurements, for example using Vernier stimuli targets for astigmatism measurement because single line patterns do not suffer from artifact problems.

Figure 15:
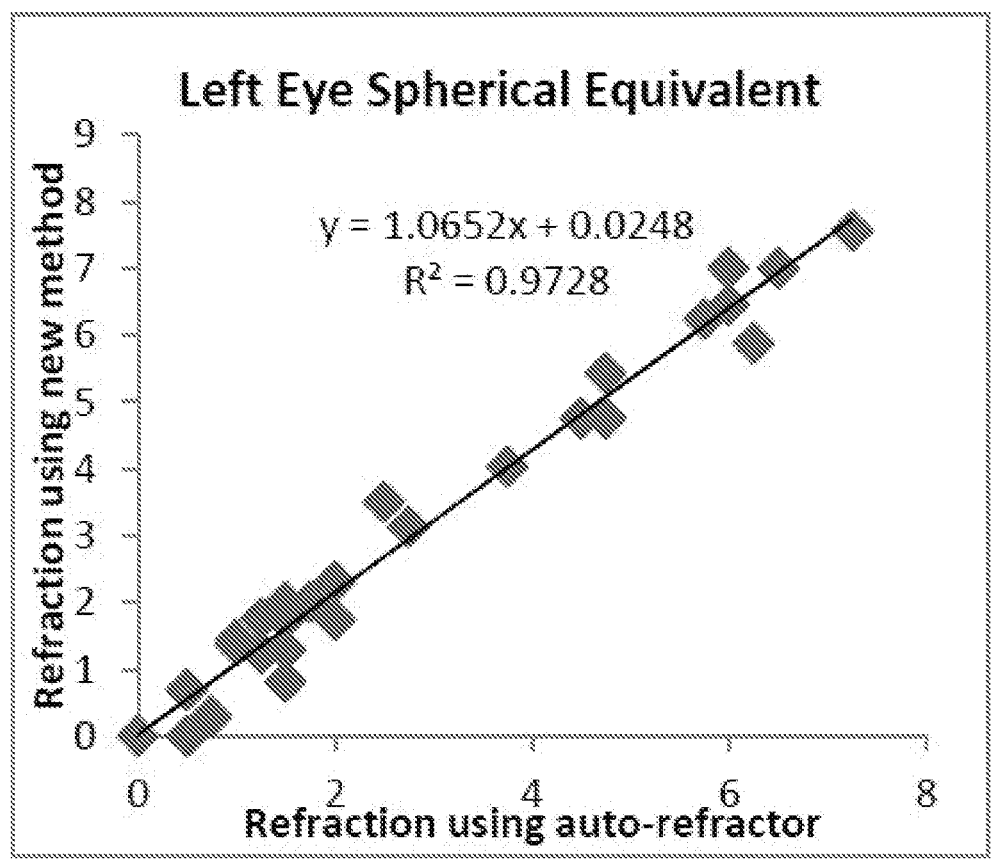
FIG. 15 illustrates left-eye test results performed on subjects using the mobile device application provided herein.
Figure 16:
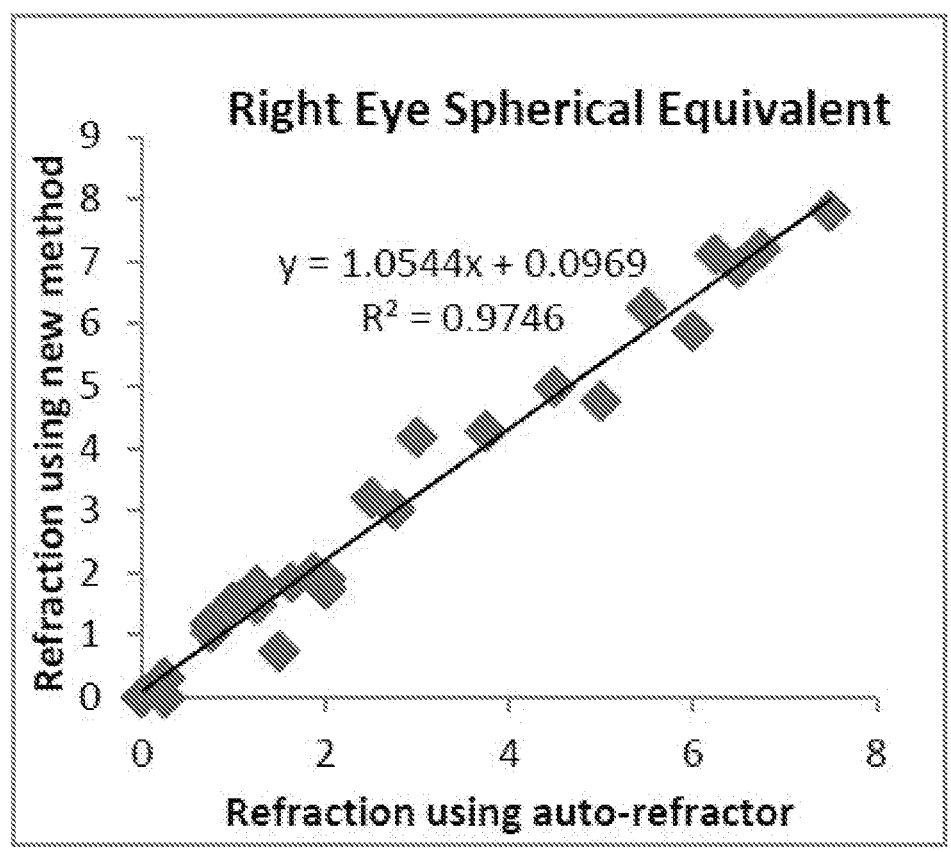
FIG. 16 illustrates right-eye test results performed on subjects using the mobile device application provided herein.

Test Data:

As illustrated in FIGS. 15 and 16, the application and method provided herein was tested on 30 subjects. Each subject had their eye refraction first measured using an auto-refractor (Topcon, RM8000B) for both eyes. They were then tested using the disclosed approach. Vernier stimuli were presented on a computer screen. The distance from the subjects to the screen was measured manually and stimulation target size was changed according to the distance. As shown in the results in FIGS. 15 and 16, the refraction measured using the approach discussed herein matched the auto-refractor results very well, with a slope of almost 1 and an R-square that was very high.

It should be noted that the steps shown throughout are merely examples for illustration, and certain other steps may be included or excluded as desired. Further, while a variety of particular orders of steps are shown in the figures herein, this ordering is merely illustrative, and any suitable arrangement of the steps may be utilized without departing from the scope of the embodiments herein. Even further, the illustrated steps may be modified in any suitable manner in accordance with the scope of the present claims.

Accordingly, techniques are described throughout that allow for measuring eye refraction using widely accessible mobile devices, such as a smart phone, tablet, and the like. The mobile device can leverage the native hardware already installed in many modern mobile devices, such as a camera, a display, and various inputs. The entire processing is performed on the mobile device itself, rather than sending data and/or captured photographs to a remote server for processing.

Advantageously, the mobile application facilitates a quick, convenient, and inexpensive way to measure eye retraction of a patient. The ability to provide objective measurements quickly and conveniently can be highly beneficial to clinicians who see large volumes of patients on a regular basis. Alternatively, the application can be used at home, for example, by patients who may be unable to visit a clinician's office for a variety of reasons, such as cost, convenience, etc. Greater accessibility to ocular screenings can help alleviate missing, inaccurate, and/or outdated diagnoses. The application is also well suited for telemedicine, which can be useful in remote, underserved areas, or for remote follow-up of treatment without the patient having to visit the doctor. Further, due to the high-resolution capabilities of modern mobile device cameras, the application can make accurate measurements that are otherwise difficult to perform using conventional methods. In addition, the application is robust in that it handles a variety of conditions and variability of distance, placement, and eye appearance between subjects and test scenarios.

While there have been shown and described illustrative embodiments that provide for a mobile device application for eye refraction measurement, it is to be understood that various other adaptations and modifications may be made within the spirit and scope of the embodiments herein. For instance, while a mobile device is frequently mentioned throughout the present disclosure, the techniques described herein may also be implemented on desktop computers or similar machines. Thus, the embodiments of the present disclosure may be modified in any suitable manner in accordance with the scope of the present claims.

The foregoing description has been directed to embodiments of the present disclosure. It will be apparent, however, that other variations and modifications may be made to the described embodiments, with the attainment of some or all of their advantages. Accordingly, this description is to be taken only by way of example and not to otherwise limit the scope of the embodiments herein.

What is claimed is:

1. A method of vision prescription measurement, the method comprising:
   automatically measuring, by an image acquisition unit installed in a mobile device, a distance between a patient and the mobile device;
   presenting, on a display of the mobile device, one or more visual targets sized and shaped to represent perfect vision, the visual targets including Vernier targets, a processor installed in the mobile device determining accurate sizes and shapes based on the measured distance;
   instructing the patient to indicate whether the patient can accurately read the visual targets and, if not, to move closer to the mobile device until the patient can accurately read the visual targets;
   automatically measuring, by the image acquisition unit installed in a mobile device, the distance between the patient and the mobile device again at a final distance at which distance the patient can accurately read the visual targets;
   calculating, by the processor, a vision prescription for the patient based on the visual targets and the final distance between the patient and the mobile device; and
   displaying, by the display, the vision prescription for the patient.

2. The method of claim 1, wherein the patient accurately reading the visual targets includes accurately identifying misaligned Vernier targets.

3. The method of claim 1, wherein automatically measuring the distance includes:
   sampling, by the processor, gyroscopic data from the mobile device and sampling images from the image acquisition unit;
   instructing, by the mobile device, the patient to rotate the mobile device;
   computing, by the processor, a rotational angle based on the sampled gyroscopic data and the rotation of the mobile device;
   tracking, by the processor, feature points across multiple images and determining feature point shifts based on the tracked feature points; and
   computing, by the processor, a pixel-to-angle ratio based on the feature point shifts and the rotational angle.

4. The method of claim 1, wherein automatically measuring the distance includes:
   capturing, by the image acquisition unit, an image of an eye of the patient;
   determining, by the processor, if an iris is present in the image;
   measuring, by the processor, a diameter of the iris; and
   computing, by the processor, the distance between the patient and the mobile device based on the measured diameter of the iris of the patient.

5. The method of claim 1, further comprising:
   prior to automatically measuring the distance, instructing, by the mobile device, the patient to create a 3D model of a face of the patient and save the 3D model to the mobile device;
   capturing a current face image of the patient by the image acquisition unit; and
   measuring, by the processor, the distance between the patient and the mobile device by comparing the current face image to the 3D model of the patient stored on the mobile device.

6. The method of claim 1, further comprising:
   prior to automatically measuring the distance, instructing, by the mobile device, the patient to create a 3D model of a face of the patient and save the 3D model to the mobile device
   capturing, by the image acquisition unit, a current face image of the patient;
   detecting, by the processor, one or more facial features on the current face image;
   calculating, by the processor, an overall inter-feature distance in pixels of each of the current face image and the 3D model;
   calculating, by the processor, an inter-feature distance ratio between the inter-feature distance of each of the current face image and the 3D model; and calculating, by the processor, the distance between the patient and the mobile device based on information in the 3D model and the inter-feature distance ratio.

7. A method of vision prescription measurement, the method comprising:
   automatically measuring, by an image acquisition unit installed in a mobile device, a distance between a patient and the mobile device;
   presenting, on a display of the mobile device, one or more visual targets sized and shaped to represent perfect vision, the visual targets including grating targets, a processor installed in the mobile device determining accurate sizes and shapes based on the measured distance;
   instructing the patient to indicate whether the patient can accurately read the visual targets and, if not, to move closer to the mobile device until the patient can accurately read the visual targets;
   automatically measuring, by the image acquisition unit installed in a mobile device, the distance between the patient and the mobile device again at a final distance at which distance the patient can accurately read the visual targets;
   calculating, by the processor, a vision prescription for the patient based on the visual targets and the final distance between the patient and the mobile device; and
   displaying, by the display, the vision prescription for the patient.

8. The method of claim 7, wherein the patient accurately reading the visual targets includes accurately identifying which of a plurality of stimuli has a grating pattern relative to the remaining plurality of stimuli that are gray patches.

9. The method of claim 7, wherein automatically measuring the distance includes:
   sampling, by the processor, gyroscopic data from the mobile device and sampling images from the image acquisition unit;
   instructing, by the mobile device, the patient to rotate the mobile device;
   computing, by the processor, a rotational angle based on the sampled gyroscopic data and the rotation of the mobile device;
   tracking, by the processor, feature points across multiple images and determining feature point shifts based on the tracked feature points; and
   computing, by the processor, a pixel-to-angle ratio based on the feature point shifts and the rotational angle.

10. The method of claim 7, wherein automatically measuring the distance includes:
    capturing, by the image acquisition unit, an image of an eye of the patient;
    determining, by the processor, if an iris is present in the image;
    measuring, by the processor, a diameter of the iris; and
    computing, by the processor, the distance between the patient and the mobile device based on the measured diameter of the iris of the patient.

11. The method of claim 7, further comprising:
    prior to automatically measuring the distance, instructing, by the mobile device, the patient to create a 3D model of a face of the patient and save the 3D model to the mobile device.

12. The method of claim 11, wherein automatically measuring the distance includes:
    capturing a current face image of the patient by the image acquisition unit; and
    measuring, by the processor, the distance between the patient and the mobile device by comparing the current face image to the 3D model of the patient stored on the mobile device.

13. The method of claim 11, wherein automatically measuring the distance includes:
    capturing, by the image acquisition unit, a current face image of the patient;
    detecting, by the processor, one or more facial features on the current face image;
    calculating, by the processor, an overall inter-feature distance in pixels of each of the current face image and the 3D model;
    calculating, by the processor, an inter-feature distance ratio between the inter-feature distance of each of the current face image and the 3D model; and
    calculating, by the processor, the distance between the patient and the mobile device based on information in the 3D model and the inter-feature distance ratio.

* * * * *

UNITED STATES PATENT AND TRADEMARK OFFICE
CERTIFICATE OF CORRECTION

PATENT NO. : 11,903,644 B2
APPLICATION NO. : 16/971981
DATED : February 20, 2024
INVENTOR(S) : Gang Luo It is certified that error appears in the above-identified patent and that said Letters Patent is hereby corrected as shown below:

In the Specification

Column 11, Line 50, "angle 9 can" should be --angle θ can--.

Signed and Sealed this
Eleventh Day of June, 2024

Katherine Kelly Vidal
*Director of the United States Patent and Trademark Office*